US011382292B2

(12) United States Patent
Pan et al.

(10) Patent No.: US 11,382,292 B2
(45) Date of Patent: Jul. 12, 2022

(54) INDETERMINATE *HELIANTHUS* PLANT

(71) Applicant: SYNGENTA PARTICIPATIONS AG, Basel (CH)

(72) Inventors: Shifeng Pan, Gilroy, CA (US); Jason Jandrew, Nipomo, CA (US)

(73) Assignee: Syngenta Participations AG, Basel (CH)

( * ) Notice: Subject to any disclaimer, the term of this patent is extended or adjusted under 35 U.S.C. 154(b) by 114 days.

(21) Appl. No.: 15/747,160

(22) PCT Filed: Jul. 22, 2016

(86) PCT No.: PCT/US2016/043600
§ 371 (c)(1),
(2) Date: Jan. 24, 2018

(87) PCT Pub. No.: WO2017/019519
PCT Pub. Date: Feb. 2, 2017

(65) Prior Publication Data
US 2018/0213741 A1 Aug. 2, 2018

Related U.S. Application Data

(60) Provisional application No. 62/197,152, filed on Jul. 27, 2015.

(51) Int. Cl.
*A01H 6/14* (2018.01)
*A01H 5/10* (2018.01)
*A01H 1/02* (2006.01)
*A01H 1/04* (2006.01)
*A01H 5/02* (2018.01)

(52) U.S. Cl.
CPC .............. *A01H 6/1464* (2018.05); *A01H 1/02* (2013.01); *A01H 1/04* (2013.01); *A01H 5/02* (2013.01); *A01H 5/10* (2013.01)

(58) Field of Classification Search
CPC ..................................................... A01H 6/1464
See application file for complete search history.

(56) References Cited

PUBLICATIONS

Kantar et al Field Crops Research vol. 155 pp. 254-264 (Year: 2014).*
Bert et al Theoretical and Applied Genetics vol. 107 pp. 181-189 (Year: 2003).*
Wieckhorst et al Theoretical and Applied Genetics vol. 121 pp. 1633-16454 (Year: 2010).*
Terzic, Zoric and Miladinovic HELIA vol. 29, No. 44, pp. 87-94 (Year: 2006).*
Kantar et al., Evaluating an interspecific *Helianthus annuus Helianthus tuberosus* population for use in a perennial sunflower breeding program. Field Crops Research, 2014, vol. 155, pp. 254-264.
International Search Report dated Oct. 31, 2016 received in International Application No. PCT/US2016/043600.
"The Biology of *Helianthus annuus* L. (Sunflower), Biology Document", Canada Food Inspection Agency, Jan. 2005, pp. 1-11 [Retreived on Sep. 29, 2016 and from http://cera-gmc-org./docs/decdocs/05-209-009.pdf] p. 6, paragraph 2, p. 7, paragraph 4.

* cited by examiner

*Primary Examiner* — David H Kruse
(74) *Attorney, Agent, or Firm* — Dale Skalla

(57) ABSTRACT

The present invention provides an interspecific *Helianthus* plant comprising a genetic determinant responsible for an indeterminate phenotype. Methods of making said plant are also provided.

6 Claims, 1 Drawing Sheet

INDETERMINATE *HELIANTHUS* PLANT

RELATED APPLICATION INFORMATION

This application is a 371 of International Application No. PCT/US2016/043600, filed Jul. 22, 2015, which claims priority to 62/197,152, filed Jul. 27, 2015, the contents of which are incorporated herein by reference herein.

FIELD OF THE INVENTION

This invention relates to a plant made from *Helianthus annuus* x *Helianthus argophyllus*. In particular, it relates to a interspecific hybrid sunflower plant comprising an indeterminate phenotype made from *H. annuus* x *H. argophyllus*.

INTRODUCTION

*Helianthus* is a genus of plants comprising about 70 species in the family Asteraceae, all of which are native to North America except three species in South America. The common name "sunflower" also applies to the popular annual species *Helianthus annuus*, the common sunflower. This and other species, notably Jerusalem artichoke (*H. tuberosus*), are cultivated in temperate regions as food crops and ornamental plants.

The pot type sunflower market is rapidly growing in North America and the rest of the world. However, the current pot sunflowers on the market suffer from several disadvantages. They are often too tall to easily fit on racks for shipment, are not well-branched and have a short flowering time.

The present application describes a new indeterminate interspecific plant species made from *Helianthus annuus* x *Helianthus argophyllus* plant which unexpectedly addresses these disadvantages.

Unlike conventional *Helianthus* plants, the plant of the present invention continues to grow new branches, shoots and flowers.

This new indeterminate species has the potential to expand the ornamental sunflower usage beyond that of pot and cut flower use so that it includes large mix containers and landscapes, thereby expanding the ornamental sunflower market as a whole.

SUMMARY OF THE INVENTION

The inventors of the present invention have developed an interspecific hybrid sunflower plant which has a surprisingly high levels of branching, high levels of continuous flowering, and an indeterminate phenotype when compared with the branching and flowering characteristics of conventional *Helianthus* plants.

The present invention relates to an interspecific *Helianthus* plant comprising a genetic determinant responsible for an indeterminate phenotype.

In one embodiment, the interspecific *Helianthus* plant of the invention is obtainable by crossing with a *Helianthus* plant comprising a genetic determinant responsible for an indeterminate phenotype, wherein a sample of representative seed of said plant comprising a genetic determinant responsible for an indeterminate phenotype is deposited under NCIMB Accession No. 42200.

The present invention provides a *Helianthus* plant comprising a genetic determinant responsible for an indeterminate phenotype, wherein said genetic determinant responsible for an indeterminate phenotype can be found in a plant grown from seed deposited under NCIMB Accession No. 42200.

The present invention also provides *Helianthus* seed comprising a genetic determinant responsible for an indeterminate phenotype, wherein said seed is obtainable from a plant grown from seed deposited under NCIMB Accession No. 42200, or progeny thereof.

The present invention provides *Helianthus* seed from a plant of the present invention.

The present invention provides a *Helianthus* plant produced by growing seed from a plant of the present invention.

In one embodiment, the plant of the invention is an interspecific plant obtainable from *H. annuus* and *H. argophyllus*.

The present invention provides a method of producing $F_1$ hybrid *Helianthus* seed of a plant of the invention comprising crossing a first parent *Helianthus* plant with a second parent *Helianthus* plant and harvesting the resultant $F_1$ hybrid *Helianthus* seed.

In one embodiment, the first *Helianthus* plant is *H. annuus* and the second *Helianthus* plant is *H. argophyllus*.

The present invention provides a seed of a plant produced by the method of the present invention.

The present invention provides a hybrid plant or its parts produced by growing said hybrid seed of the present invention.

The present invention provides seed comprising a genetic determinant responsible for an indeterminate phenotype produced from the hybrid plant of the present invention.

The present invention provides viable *Helianthus* seed deposited under NCIMB Accession No. 42200 and plants grown from said deposited seed and the progeny thereof.

BRIEF DESCRIPTION OF THE DRAWING

A typical plant of the invention is illustrated in FIG. 1.

DETAILED DESCRIPTION OF THE INVENTION

The present invention provides a *Helianthus* plant comprising a genetic determinant responsible for an indeterminate phenotype.

A typical plant of the invention is illustrated in FIG. 1.

In one embodiment the *Helianthus* plant of the invention is interspecific, obtainable by crossing a *Helianthus* plant with another *Helianthus* plant comprising a genetic determinant responsible for an indeterminate phenotype, wherein a sample of representative seed of said plant comprising a genetic determinant responsible for the indeterminate phenotype is deposited under NCIMB Accession No. 42200. In one embodiment, the indeterminate phenotype is dominant.

In one embodiment, the plant of the invention is an interspecific plant made from *H. annuus* and *H. argophyllus*.

In one embodiment, the plant of the invention is an interspecific plant made from *Helianthus debilis* and another *Helianthus* plant.

In one embodiment, the *Helianthus* plant of the invention is less than 90 cm in height, more preferably less than 80 cm, more preferably less than 70 cm in height.

In one embodiment, the *Helianthus* plant of the invention is more than 60 cm in height.

In one embodiment, the height of the corresponding seed parent line used to make the plant of the invention is between 35 cm and 45 cm.

In one embodiment, the *Helianthus* plant of the invention has at least 80 flowers, more preferably at least 90 flowers, more preferably at least 100 flowers, more preferably at least 110 flowers.

In one embodiment, the *Helianthus* plant of the invention has between 80 and 120 flowers.

In one embodiment, the *Helianthus* plant of the invention has a width of between 140 cm to 160 cm.

In one embodiment, the *Helianthus* plant of the invention has a secondary flower diameter of at least 14 cm, more preferably at least 15 cm, most preferably at least 16 cm.

In one embodiment, the *Helianthus* plant of the invention has a secondary flower diameter of between 15 cm to 17 cm.

In one embodiment, the plant height, number of flowers, plant width, and flower diameter is measured under typical environmental conditions as described herein. In one embodiment, these measurements are taken from the finished plant.

The plant of the invention is well branched and early to bloom as defined herein.

In one embodiment, the *Helianthus* plant of the invention has pollenless flowers. A pollenless flower has no visible pollen when grown in the absence of stressful conditions such as low water and/or low or no fertilizer.

In one embodiment, the *Helianthus* plant of the invention has a day neutral flowering response.

In one embodiment, the *Helianthus* plant according to the present invention is an annual plant.

The present invention provides a *Helianthus* plant comprising a genetic determinant responsible for an indeterminate phenotype, wherein said genetic determinant responsible for an indeterminate phenotype can be found in a plant grown from seed deposited under NCIMB Accession No. 42200.

The present invention provides *Helianthus* seed comprising a genetic determinant responsible for an indeterminate phenotype, wherein said seed is obtainable from a plant grown from seed deposited under NCIMB Accession No. 42200, or progeny thereof.

The present invention provides *Helianthus* seed comprising a genetic determinant responsible for an indeterminate phenotype, wherein said seed has a pedigree which includes the plant *Helianthus* Interspecific Hybrid SUO22=SUL1, and wherein representative seed of said plant has been deposited under NCIMB Accession No. 42200.

The present invention provides a *Helianthus* seed comprising a genetic determinant responsible for an indeterminate phenotype, wherein said genetic determinant is present in *Helianthus* Interspecific SUO22=SUL1, a representative sample of seed which is deposited at NCIMB under Accession No. NCIMB 42200, or in a progeny or ancestor thereof comprising said genetic determinant responsible for an indeterminate phenotype.

In one embodiment, the plant of the invention is an elite *Helianthus* plant comprising a genetic determinant responsible for an indeterminate phenotype.

In one embodiment, *Helianthus* seed from a plant of the invention comprises a genetic determinant responsible for an indeterminate phenotype.

The present invention provides a *Helianthus* plant produced by growing the seed of the present invention.

In one embodiment, the *Helianthus* plant of the invention is a hybrid. In one embodiment, the hybrid *Helianthus* plant of the invention is male sterile.

The present invention provides a tissue culture of cells produced from a *Helianthus* plant of the present invention, wherein said cells of the tissue culture are produced from a plant part selected from the group consisting of seed, leaf, pollen, embryo, cotyledon, hypocotyl, meristematic cell, root, root tip, pistil, anther, flower, stem, and petiole.

The present invention provides a *Helianthus* plant of the present invention regenerated from tissue culture.

The present invention provides an ovule of the *Helianthus* plant of the present invention.

The present invention provides a method of producing $F_1$ hybrid *Helianthus* seed comprising crossing a first parent *Helianthus* plant with a second parent *Helianthus* plant and harvesting the resultant $F_1$ hybrid *Helianthus* seed.

In one embodiment, the first parent plant is a dwarf plant and the second parent plant is a plant of the species *Helianthus argophyllus* comprising a genetic element responsible for an indeterminate phenotype. In one embodiment, the dwarf plant is the CMS female parent. In one embodiment, the female parent is a yellow and red bicolor dwarf plant. In one embodiment, the dwarf plant is the male parent. A dwarf plant is typically about 38 cm high when grown in a pot in the greenhouse under typical environmental conditions.

The present invention further relates to a method of producing the said *Helianthus* plant and seed by crossing a plant of the instant invention with another *Helianthus* plant. The invention also relates to the transfer or introgression of the genetic determinant into genera other than *Helianthus*.

In order to transfer the heritable genetic determinant to another plant, backcross breeding can be used. For this a desirable homozygous cultivar or inbred is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

A suitable donor parent for the genetic determinant responsible for an indeterminate phenotype according to the present invention may be the *Helianthus* plant *Helianthus* Interspecific Hybrid SUO22=SUL1, representative seeds of which have been deposited at NCIMB (Ferguson Building, Craibstone Estate, Bucksburn, Aberdeen AB219YA, Scotland) under NCIMB 42200 on Jan. 10, 2014.

Accordingly, the person skilled in the art of *Helianthus* breeding, based on the description of the present invention and in possession of *Helianthus* plant *Helianthus* Interspecific Hybrid SUO22=SUL1, representative seed of which is deposited under accession Number NCIMB 42200, has no difficulty transferring the genetic determinant The present invention provides hybrid seed produced by the method of the present invention.

The present invention provides a plant of the invention or its parts, including cut flowers, produced by growing seed of the present invention. In one embodiment, the plant of the invention is used in combination mix containers.

In one embodiment, the plant of the invention can be propagated by vegetative means.

The present invention provides seed comprising a genetic determinant responsible for an indeterminate phenotype produced from the hybrid plant of the present invention.

The present invention provides viable *Helianthus* seeds deposited under NCIMB Accession No. 42200 and plants grown from said deposited seeds and the progeny thereof, wherein the progeny contain the genetic determinant for the indeterminate phenotype.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants.

As used herein, the term "breeding", and grammatical variants thereof, refer to any process that generates a progeny individual. Breeding can be sexual or asexual, or any combination thereof. Exemplary non-limiting types of breeding include crossing, selfing, doubled haploid derivative generation, polyploidization and combinations thereof. The phenotype of the flower of the present invention can be readily and stably transferred by breeding to progeny.

As used herein, the term "hybrid" in the context of plant breeding refers to a plant that is the offspring of genetically dissimilar parents produced by crossing plants of different lines or breeds or species, including but not limited to the cross between two inbred lines.

A "cultivated *Helianthus* plant" or an "elite *Helianthus* plant" is understood within the scope of the invention to refer to a plant that is no longer in the natural state but has been developed by human care and for human use and/or consumption. An example of a cultivated plant or an elite plant is *Helianthus* Interspecific Hybrid Yellow Dark Centre 70052828 (SUO22=SUL1), representative seed of which is deposited under accession Number NCIMB 42200.

A "finished plant" is defined as a plant which has just started flowering. Typically, flowering starts at around 85 to 90 days from sowing (12 to 13 weeks) when grown under typical environmental conditions as described herein.

A "well branched plant" is defined as a plant which has 6 to 8 branches per plant in the pot at flowering time. Conventional pot type *Helianthus* plants only have 1 major stem per plant in pot.

An early to bloom plant is defined as a plant which blooms in about 85 to 90 days, when grown under typical environmental conditions as described herein.

Typical environmental conditions for growing a plant of the invention are 14 to 16 hours of daylight and average daily temperature of 27 to 29 degrees Celsius, from 21 days after sowing in early spring to late fall in California. Unless otherwise stated, a plant of the invention displays the stated phenotype when grown under these typical environmental conditions.

An indeterminate plant is defined as a plant which is continually branching from when the first flower appears, continually has new shoots appearing, and is continually flowering when grown under the typical environmental conditions as described herein.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, callus, and the like.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the $F_1$, the $F_2$, or any subsequent generation.

"Trait" is understood within the scope of the invention to refer to a characteristic or phenotype. A trait may be inherited in a dominant or recessive manner, and may be monogenic or polygenic.

"Dominant" is understood within the scope of the invention to refer to an allele which determines the phenotype when present in the heterozygous or homozygous state.

A "recessive" allele is only displayed when present in the homozygous state.

Seed Deposit Details

SEED DEPOSIT DETAILS

Seed of the variety *Helianthus* Interspecific Hybrid SUO22=SUL1 made from *H. annuus* and *H. argophyllus* has been deposited and accepted under the terms of the Budapest Treaty on Jan. 10, 2014 at the NCIMB, Craibstone, Aberdeen, UK under number NCIMB 42200.

The seed deposit was made in the name of Syngenta Participations AG, Basel 4002, Switzerland.

EXAMPLES

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

Example 1

Parent Pedigree

Junior is a commercial cytoplasm sterile hybrid, and it was used as a female plant to cross with a pollen plant used in Syngenta's breeding program which had been inbred for 4 generations. This cross was made in September, 2008.

The pedigree for the pollen parent was developed from an *H. argophyllus* variety used in Syngenta's breeding program. It was planted in the field in May 2008 at the premises of Syngenta in Gilroy, Calif. and open pollinated (OP) seeds were collected from selected plants in the field. The harvested OP seeds were planted in the greenhouse in March, 2008 to provide 75 plants for a trial. A single plant was selected from the trial. Self seeds were harvested from this plant and planted in Gilroy in the greenhouse in September, 2009. A plant was selected from the population, and crossed to above female parent Junior. This single plant was further developed into a true inbred line for making an interspecific hybrid. This hybrid SUO22=SUL1 was trialed and evaluated in 2010 and 2011 in several locations belonging to Syngenta, both in Gilroy and in Enkhuizen, the Netherlands, in the greenhouse and in the field.

Example 2

Plant Measurement Data

Plant measurement data was obtained from a pollen parent line *H. argophyllus*, a seed parent line *H. annuus*, and SUO22=SUL1. The measurements taken are shown in the tables below.

| Characteristics | Seed parent line H. annuus | Pollen parent line H. argophyllus | SU022 = SUL1 |
|---|---|---|---|
| Quantity of inflorescences per plant: | 4 | 6 | 6 |
| FOLIAGE | | | |
| MATURE, leaf color, upper surface: | 147A | 147A | 147A |
| Lower surface color: | 147B | 147B | 147B |
| Shape: | cordate | cordate | cordate |
| Base shape: | cordate | cordate | cordate |
| Apex shape: | abruptly acute | abruptly acute | abruptly acute |
| Margin: | crenate | crenate | crenate |
| Depth of margin indentation: (cm): | 0.2 | 0.2 | 0.2 |
| Texture, upper surface: | puberulous | pilose | puberulous |
| Color of veins, upper surface: | 145D | 145D | 145D |
| Color of veins, lower surface: | 145D | 145D | 145D |
| Petiole | | | |
| Texture: | hirsute | hirsute | hirsute |
| STEM | | | |
| Color of stem: | 145C | 145B | 145C |
| Texture: | hirsute | hirsute | hirsute |
| BUD (just when opening/showing color) | | | |
| Color: | 147A | 137C | 143C |
| Ray florets: | | | |
| Average quantity of florets: | 36 | 19 | 37 |
| Color of florets, upper surface: | 9A | 9A | 9A |
| lower surface: | 9B | 9A | 9B |
| Shape: | acute | obtuse | acute |
| Apex shape: | entire | entire | entire |

Color measurements are recorded using the Royal Horticultural Society (RHS) scale. Plant height, width and secondary flower diameter data was also recorded for SUL22=SUL1. The total number of flowers and the average per plant were recorded for SUL22=SUL1 and sunflower "Ballad". Plant height and the average height per plants was recorded for sunflower "Ballad". The measurements taken are shown in the tables below.

| SUL22 = SUL1 GILROY ||||
|---|---|---|---|
| Plant # | Height (cm) | Width (cm) | Secondary Flower Diameter (cm) |
| 1 | 96.3 | 185 | 18 |
| 2 | 97 | 142 | 16.5 |
| 3 | 88 | 161 | 17.3 |
| 4 | 90 | 152 | 17 |
| 5 | 92 | 147 | 15.7 |
| 6 | 96 | 158 | 17.2 |
| 7 | 103 | 147 | 16 |
| 8 | 93 | 171 | 16.7 |
| 9 | 98 | 167 | 16.4 |
| 10 | 88 | 154 | 16.6 |
| 11 | 92 | 139 | 16.3 |
| 12 | 83 | 146 | 16.1 |
| 13 | 92 | 139 | 17.3 |
| 14 | 83 | 147 | 16.5 |
| 15 | 87 | 136 | 16.6 |
| 16 | 90 | 165 | 16.3 |
| 17 | 88 | 157 | 16.3 |
| 18 | 100 | 149 | 16.6 |
| 19 | 87 | 147 | 16.1 |
| 20 | 87 | 143 | 16.7 |
| 21 | 83 | 148 | 17.4 |
| 22 | 93 | 162 | 17.1 |
| 23 | 86 | 131 | 17.3 |
| 24 | 91 | 156 | 16.8 |
| Av: | 90.9 | 152.0 | 16.7 |

| SUL22 = SUL1 GILROY |||
|---|---|---|
| Plant # | Total # of Flowers | Average per Plant |
| 1 | 113 | 105 |
| 2 | 99 | |
| 3 | 81 | |
| 4 | 108 | |
| 5 | 124 | |

| Sunflower Ballad GILROY |||
|---|---|---|
| Plant # | Total # of Flowers | Average per Plant |
| 1 | 32 | 37 |
| 2 | 40 | |
| 3 | 41 | |
| 4 | 33 | |
| 5 | 39 | |

| Sunflower Ballad GILROY |||
|---|---|---|
| Plant # | Height (cm) | Average Height (cm) |
| 1 | 48 | 46.9 |
| 2 | 48 | |
| 3 | 41 | |
| 4 | 51 | |
| 5 | 46.5 | |

| | Seed Parent Line | | | | | | | | | |
|---|---|---|---|---|---|---|---|---|---|---|
| | 1 | 2 | 3 | 4 | 5 | 6 | 7 | 8 | 9 | 10 |
| Total plant height (cm) | 41.6 | 43.4 | 40.1 | 43 | 40.8 | 42.4 | 41.5 | 43.4 | 42.6 | 42.5 |
| plant width (cm) | 33.5 | 32.7 | 32.9 | 37.3 | 28.9 | 35.3 | 33 | 34.6 | 28.2 | 27.8 |
| Foliage | | | | | | | | | | |
| Length (cm) | 12.2 | 10.9 | 10.8 | 10.7 | 11.7 | 12 | 11 | 11.6 | 12.5 | 10.9 |
| width (cm) | 10 | 8.8 | 9 | 8.9 | 9.7 | 10.1 | 9.3 | 10 | 10.3 | 8.9 |
| Petiole | | | | | | | | | | |
| Length (cm) | 7.7 | 6.3 | 6.7 | 6.8 | 7 | 7.5 | 6.4 | 6.8 | 8 | 6.7 |
| diameter (cm) | 0.4 | 0.4 | 0.4 | 0.4 | 0.4 | 0.4 | 0.4 | 0.4 | 0.4 | 0.4 |
| Stem: | | | | | | | | | | |
| diameter (cm) | 1.1 | 1 | 0.9 | 1 | 1 | 1 | 1.2 | 1 | 1 | 1 |
| length of internodes (cm) | 1.3 | 2.5 | 2.2 | 1.7 | 1.8 | 1.5 | 1.2 | 2 | 1.8 | 2.1 |
| Bud: | | | | | | | | | | |
| length (cm) | 2.3 | 2 | 2.1 | 2 | 2 | 2 | 1.8 | 2 | 1.5 | 2 |
| width (cm) | 3 | 2.4 | 2.5 | 2.5 | 2.5 | 2.5 | 2.7 | 2.8 | 2.3 | 2.6 |
| Immature inflorescence: | | | | | | | | | | |
| total diameter (cm) | 10.5 | 9.5 | 10.1 | 10 | 9.9 | 9.7 | 10.5 | 10.6 | 10.9 | 10.6 |
| diamter of 'disc' | 2.3 | 3 | 3 | 3 | 2.8 | 3.1 | 3.4 | 3.3 | 3.5 | 2.9 |
| mature inflorescence: | | | | | | | | | | |
| total diameter (cm) | 14.6 | 14.4 | 14.5 | 14.6 | 13.4 | 13.8 | 14.6 | 14.2 | 14.9 | 13.2 |
| depth of inflorescence head (cm) | 2.1 | 1.9 | 2.2 | 2.5 | 2.3 | 2.1 | 2.5 | 2.3 | 2.3 | 2.3 |
| disc diameter | 5.2 | 6 | 5.1 | 6.1 | 5.2 | 5 | 5.9 | 5.6 | 5.7 | 5.1 |
| Ray florets | | | | | | | | | | |
| length (cm) | 5.4 | 5.2 | 5 | 5.3 | 4.7 | 4.9 | 5 | 5.1 | 4.7 | 4.5 |
| width (cm) | 1.5 | 1.5 | 1.5 | 1.5 | 1.5 | 1.4 | 1.6 | 1.6 | 1.5 | 1.4 |
| Disc florets | | | | | | | | | | |
| length (cm) | 1.1 | 1.1 | 1 | 1.1 | 1 | 1 | 1 | 1.1 | 1.1 | 1.1 |
| width (cm) | 0.4 | 0.3 | 0.3 | 0.3 | 0.3 | 0.3 | 0.3 | 0.3 | 0.3 | 0.3 |

| | New Hybrid Line SUO22 = SUL1 | | | | | | | | | |
|---|---|---|---|---|---|---|---|---|---|---|
| | 1 | 2 | 3 | 4 | 5 | 6 | 7 | 8 | 9 | 10 |
| Total plant height (cm) | 76 | 78 | 74 | 69 | 73 | 76 | 71 | 79 | 70 | 72 |
| plant width (cm) | 35 | 35 | 40 | 3 | 42 | 43 | 39 | 34 | 38 | 35 |
| Foliage | | | | | | | | | | |
| Length (cm) | 11.4 | 11.7 | 13.4 | 12.7 | 12.6 | 12 | 13.3 | 12.7 | 11.7 | 11.9 |
| width (cm) | 10.6 | 9.7 | 10.5 | 9.9 | 9.5 | 9.4 | 11.4 | 10 | 8.5 | 9.6 |
| Petiole | | | | | | | | | | |
| Length (cm) | 7.7 | 5.9 | 6.5 | 6.6 | 5.8 | 6.1 | 6.5 | 6.6 | 4.5 | 6.5 |
| diameter (cm) | 0.4 | 0.4 | 0.5 | 0.4 | 0.5 | 0.4 | 0.5 | 0.5 | 0.5 | 0.5 |
| Stem: | | | | | | | | | | |
| diameter (cm) | 1.2 | 1.1 | 1.2 | 1 | 1.3 | 1.2 | 1.2 | 1.2 | 1 | 1.2 |
| length of internodes (cm) | 3.5 | 3.4 | 3.8 | 5.2 | 3.6 | 2.8 | 3.7 | 4.5 | 2.5 | 3.2 |
| Bud: | | | | | | | | | | |
| length (cm) | 2.1 | 2 | 2.3 | 2 | 2.8 | 2.3 | 2.6 | 2.2 | 2.3 | 2 |
| width (cm) | 5 | 3.4 | 4.1 | 4.8 | 5 | 4.9 | 5 | 5 | 4.2 | 3.9 |
| Immature inflorescence: | | | | | | | | | | |
| total diameter (cm) | 11.6 | 9.7 | 10.2 | 10.4 | 10.2 | 9.4 | 11.7 | 10.1 | 11.6 | 9.9 |
| diamter of 'disc' | 4 | 2 | 3.5 | 3.3 | 3 | 3 | 3.2 | 3.5 | 3.9 | 2.9 |
| mature inflorescence: | | | | | | | | | | |
| total diameter (cm) | 14.8 | 13.5 | 14.9 | 16 | 12.6 | 14.6 | 14.3 | 15.8 | 14.9 | 12.5 |
| depth of inflorescence head (cm) | 2.5 | 2 | 2.4 | 2.3 | 1.8 | 2.2 | 2.3 | 2.5 | 2.3 | 1.6 |
| disc diameter | 5.5 | 4.8 | 5.7 | 5.2 | 4.8 | 5.4 | 5 | 5.5 | 5.6 | 4.5 |
| Ray florets | | | | | | | | | | |
| length (cm) | 5.8 | 5.2 | 5.6 | 5.4 | 4.7 | 5.7 | 5.5 | 5.9 | 5.7 | 4.6 |
| width (cm) | 2 | 1.9 | 2 | 2 | 1.2 | 2 | 1.9 | 2.1 | 2.1 | 1.2 |

-continued

| | New Hybrid Line SUO22 = SUL1 | | | | | | | | | |
|---|---|---|---|---|---|---|---|---|---|---|
| | 1 | 2 | 3 | 4 | 5 | 6 | 7 | 8 | 9 | 10 |
| Disc florets | | | | | | | | | | |
| length (cm) | 1.1 | 1.1 | 0.9 | 0.9 | 1 | 1 | 1 | 1 | 1 | 0.9 |
| width (cm) | 0.3 | 0.3 | 0.3 | 0.3 | 0.3 | 0.3 | 0.3 | 0.4 | 0.3 | 0.3 |

| | Ballad | | | | | | | | | |
|---|---|---|---|---|---|---|---|---|---|---|
| | 1 | 2 | 3 | 4 | 5 | 6 | 7 | 8 | 9 | 10 |
| Total plant height (cm) | 35 | 33 | 28 | 34 | 30 | 30 | 32 | 25 | 33 | 29 |
| plant width (cm) | 25 | 25 | 25 | 27 | 24 | 25 | 26 | 27 | 27 | 28 |
| Foliage | | | | | | | | | | |
| Length (cm) | 11.1 | 11.9 | 10.2 | 10.6 | 10.1 | 11.7 | 11.4 | 11 | 11.1 | 11.2 |
| width (cm) | 8.8 | 9.5 | 9.5 | 9.4 | 9.2 | 9.5 | 9.3 | 9.5 | 9.2 | 8.7 |
| Petiole | | | | | | | | | | |
| Length (cm) | 6.8 | 7 | 5.3 | 6.3 | 5.8 | 5.3 | 6.4 | 6 | 6 | 6.8 |
| diameter (cm) | 0.5 | 0.4 | 0.4 | 0.5 | 0.5 | 0.4 | 0.5 | 0.5 | 0.5 | 0.4 |
| Stem: | | | | | | | | | | |
| diameter (cm) | 1.1 | 1 | 1 | 1.2 | 1 | 1 | 1.2 | 1.1 | 1.3 | 1.1 |
| length of internodes (cm) | 2.5 | 3 | 2 | 1 | 1 | 2 | 1.4 | 1.7 | 1.2 | 1 |
| Bud: | | | | | | | | | | |
| length (cm) | 2.3 | 2 | 1.9 | 2.4 | 2 | 1.9 | 1.9 | 1.6 | 2.3 | 2.8 |
| width (cm) | 3.5 | 4 | 3.1 | 2.5 | 2.7 | 2 | 1.5 | 2.2 | 2.4 | 3 |
| Immature inflorescence: | | | | | | | | | | |
| total diameter (cm) | — | 7 | — | 7.6 | 6.6 | — | 8.9 | 6.4 | 7.5 | 7.5 |
| diamter of 'disc' | — | 3 | — | 2 | 2.4 | — | 3.4 | 2.5 | 2.6 | 3 |
| mature inflorescence: | | | | | | | | | | |
| total diameter (cm) | 13.9 | 14.2 | 15.5 | 14.9 | 14.2 | 15.5 | 14.3 | 14.7 | 14.6 | 14.1 |
| depth of inflorescence head (cm) | 2.5 | 3.1 | 3 | 2.8 | 3 | 3 | 2.8 | 3 | 3 | 2.6 |
| disc diameter | 7 | 6.7 | 6.8 | 6.3 | 6.5 | 7.1 | 6.5 | 6.8 | 7 | 6.5 |
| Ray florets | | | | | | | | | | |
| length (cm) | 4.6 | 4.8 | 4.5 | 4.8 | 4.6 | 5.1 | 4.9 | 5 | 4.9 | 4.4 |
| width (cm) | 1.6 | 1.7 | 1.7 | 1.9 | 1.8 | 1.9 | 1.8 | 1.9 | 1.9 | 1.7 |
| Disc florets | | | | | | | | | | |
| length (cm) | 1 | 0.8 | 0.8 | 0.9 | 0.8 | 0.8 | 0.8 | 0.9 | 0.9 | 0.9 |
| width (cm) | 0.3 | 0.3 | 0.3 | 0.3 | 0.3 | 0.3 | 0.3 | 0.3 | 0.3 | 0.3 |

The invention claimed is:

1. An interspecific *Helianthus* plant designated SUO22=SUL1 representative seed deposited under NCIMB Accession No. 42200.

2. The interspecific *Helianthus* plant of claim 1 wherein said plant is made from *H. annuus* and *H. argophyllus*.

3. A method of producing hybrid *Helianthus* seed comprising crossing a first parent *Helianthus* plant with a second parent *Helianthus* plant and harvesting the resultant hybrid *Helianthus* seed, wherein the first parent *Helianthus* plant or the second parent *Helianthus* plant is the plant of claim 1.

4. A hybrid *Helianthus* seed produced by the method of claim 3, wherein the female parent is the interspecific *Helianthus* plant designated SUO22=SUL1.

5. A method of producing a hybrid *Helianthus* plant or its parts, said method comprising growing a hybrid seed produced by the method of claim 3.

6. A viable *Helianthus* seed designated SUO22=SUL1 deposited under NCIMB Accession No. 42200.

* * * * *